(12) United States Patent
Greif et al.

(10) Patent No.: US 6,620,833 B1
(45) Date of Patent: Sep. 16, 2003

(54) SUBSTITUTED BENZIMIDAZOLES, PRODUCTION AND USE THEREOF AS AGENTS FOR COMBATING PARASITIC PROTOZOAS

(75) Inventors: Gisela Greif, Remagen (DE); Axel Haberkorn, Wuppertal (DE); Bernd Baasner, Bergisch Gladbach (DE); Folker Lieb, Leverkusen (DE); Albrecht Marhold, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/743,440

(22) PCT Filed: Jul. 5, 1999

(86) PCT No.: PCT/EP99/04650

§ 371 (c)(1),
(2), (4) Date: Jan. 9, 2001

(87) PCT Pub. No.: WO00/04022

PCT Pub. Date: Jan. 27, 2000

(30) Foreign Application Priority Data

Jul. 16, 1998 (DE) .......................... 198 31 985

(51) Int. Cl.[7] .................. A61K 31/4184; C07D 487/04
(52) U.S. Cl. .................. 514/394; 548/302.1
(58) Field of Search ............. 548/302.1; 514/394

(56) References Cited

U.S. PATENT DOCUMENTS

| | | | |
|---|---|---|---|
| 3,418,318 A | 12/1968 | Lambie et al. ........... | 260/247.5 |
| 3,472,865 A | 10/1969 | Newbold et al. ......... | 260/309.2 |
| 3,576,818 A | 4/1971 | Samuel et al. ........... | 260/309.2 |
| 3,738,994 A | 6/1973 | Fisher ....................... | 260/309.2 |
| 4,536,502 A | 8/1985 | Giraudon et al. .......... | 514/227 |
| 4,622,323 A | 11/1986 | Giraudon et al. .......... | 514/228 |
| 5,331,003 A | 7/1994 | O'Doherty ................. | 514/394 |
| 5,482,956 A | 1/1996 | Lunkenheimer et al. .... | 514/394 |

FOREIGN PATENT DOCUMENTS

| | | |
|---|---|---|
| DE | 2040175 | 2/1972 |
| EP | 0 811 826 | 5/1986 |
| EP | 0 239 508 | 9/1987 |
| EP | 0 260 744 | 12/1992 |
| GB | 1350528 | 4/1974 |

*Primary Examiner*—Patricia L. Morris
(74) *Attorney, Agent, or Firm*—Susan M. Pellegrino

(57) ABSTRACT

The present invention relates to new substituted benzimidazoles, their preparation and their use as agents against parasitic protozoa. The active compounds are characterized by the following formula (I):

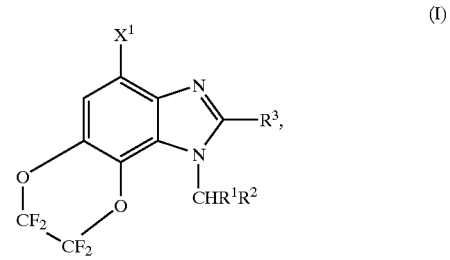

in which
$X^1$ represents chlorine or bromine,
$R^1$ represents hydrogen or $C_{1-4}$-alkyl,
$R^3$ represents fluoroalkyl,
$R^2$ represents the radical

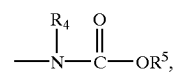

$R^4$ represents alkyl or substituted phenyl,
$R^5$ represents alkyl.

4 Claims, No Drawings

SUBSTITUTED BENZIMIDAZOLES, PRODUCTION AND USE THEREOF AS AGENTS FOR COMBATING PARASITIC PROTOZOAS

The present invention relates to new substituted benzimidazoles, their preparation and their use as agents against parasitic protozoa.

The present invention further relates to mixtures of these compounds with polyether antibiotics or synthetically prepared coccidiosis agents in compositions for the control of parasitic protozoa, in particular coccidia.

Substituted benzimidazoles and their use as insecticides, fungicides and herbicides have already been disclosed (EP-OS [European Published Specification] 87 375, 152 360, 181 826, 239 508, 260 744, 266 984, U.S. Pat. Nos. 3,418,318, 3,472,865, 3,576,818, 3,728,994).

Halogenated benzimidazoles and their action as anthelmintics, coccidiostatics and pesticides have already been disclosed (DE-OS [German Published Specification] 2 047 369, DE-OS [German Published Specification] 4 237 617). Mixtures of nitro-substituted benzimidazoles and polyether antibiotics have been disclosed as coccidiosis agents (U.S. Pat. No. 5,331,003). In all cases their action is still not satisfactory.

Coccidiosis is a disorder which is caused by single-cell parasites (protozoa). It can cause great losses, in particular when raising poultry. In order to avoid these, the stocks are treated prophylactically with coccidiosis agents. Owing to the development of resistance to the agents employed, serious problems already occur shortly after introduction of the agents. By means of the use of chemically completely new coccidiosis agents, in particular combinations, it is possible, on the other hand, to control even polyresistant parasite strains.

The benzimidazoles of the formula (I)

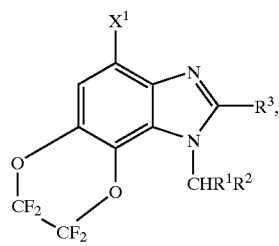

in which
$X^1$ represents chlorine or bromine,
$R^1$ represents hydrogen or $C_{1-4}$-alkyl,
$R^3$ represents fluoroalkyl,
$R^2$ represents the radical

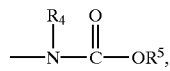

$R^4$ represents alkyl or substituted phenyl,
$R^5$ represents alkyl,
are new and especially suitable for combating a parasitic protozoa.

The benzimidazoles of the formula (I)

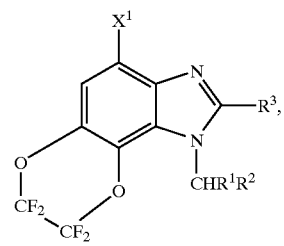

in which
$X^1$ represents chlorine or bromine
$R^1$ represents hydrogen or $C_{1-4}$-alkyl,
$R^3$ represents fluoroalkyl,
$R^2$ represents the radical

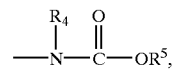

$R^4$ represents alkyl or substituted phenyl,
$R^5$ represents alkyl,
are prepared by a process in which
1H-benzimidazoles of the formula (II)

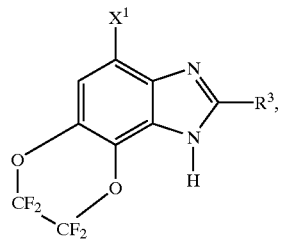

in which
$X^1$ and $R^3$ have the meaning indicated above.
are reacted with an alkylating agent of the formula (III)

in which
A represents a suitable leaving group,
$R^1$ and $R^2$ have the meaning indicated above,
if appropriate in the presence of diluents and/or reaction auxiliaries.

The compounds of the formula (I) can optionally be present in differing compositions as geometrical and/or optical isomers or regioisomers or isomer mixtures thereof, depending on the type and number of substituents. Both the pure isomers and the isomer mixtures are claimed according to the invention.

Formula (I) provides a general definition of the substituted benzimidazoles according to the invention. Preferred compounds of the formula (I) are those in which
$X^1$ represents chlorine or bromine,
$R^1$ represents hydrogen or $C_{1-4}$-alkyl such as methyl, ethyl, i-propyl, $R^2$ represents the radical

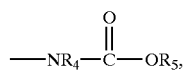

$R^4$ represents $C_{1-6}$-alkyl such as methyl, ethyl, n-propyl, i-propyl, n-butyl, s-butyl, i-butyl, t-butyl, n-pentyl, n-hexyl, cyclohexyl, as well as substituted phenyl. Possible substituents of the phenyl ring in this case are: $C_{1-4}$-alkyl, in particular methyl, $C_{1-4}$-halogenoalkyl, in particular trifluoromethyl, halogen, nitro, $C_{1-4}$-alkoxy, in particular methoxy, $C_{1-4}$-halogenoalkoxy, in particular trifluoromethoxy, methylenedioxy, ethylenedioxy, which for their part can be halogen-substituted, $R^5$ represents $C_{1-4}$-alkyl, in particular methyl or ethyl, $R^3$ represents perfluoro-$C_{1-4}$-alkyl, in particular trifluoromethyl.

Particularly preferred compounds of the formula (I) are those in which $X^1$ represents chlorine or bromine, $R^1$ represents hydrogen, $R^2$ represents the radical

$R^4$ represents $C_{1-6}$-alkyl, $R^5$ represents methyl or ethyl, $R^3$ represents trifluoromethyl.

If, for example, benzimidazole is used for the preparation of the compounds of the formula (I) according to the invention, the course of reaction of the preparation process can be represented by the following equation:

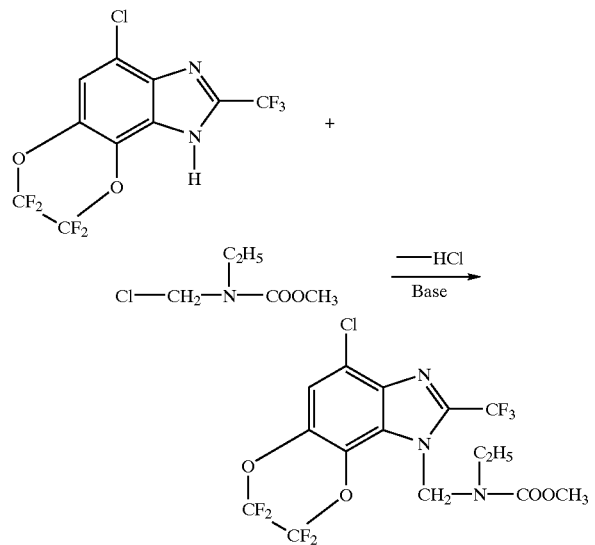

Formula (II) provides a general definition of the 1H-benzimidazoles needed as starting substances for carrying out the preparation process. In this formula (II), $X^1$ and $R^3$ preferably represent those radicals which have already been mentioned as preferred for these substituents in connection with the description of the compounds of the formula (I) according to the invention.

The 1H-benzimidazoles of the formula (II) are known or obtainable in analogy to known processes (cf., for example, J. Amer. Chem. Soc. 75, 1292 [1953] U.S. Pat. No. 3,576, 818).

Formula (III) provides a general definition of the alkylating agents furthermore necessary as starting materials for carrying out the preparation process. In this formula (III), $R^1$ and $R^2$ preferably represent those radicals which have already been mentioned as preferred for these substituents in connection with the description of the substances of the formula (I) according to the invention.

A represents a leaving radical customary in alkylating agents, preferably halogen, in particular chlorine, bromine or iodine or alkylsulphonyloxy, alkoxysulphonyloxy or arylsulphonyloxy, each of which is optionally substituted, such as, in particular, methanesulphonyloxy, trifluoromethanesulphonyloxy, methoxysulphonyloxy, ethoxysulphonyloxy or p-toluenesulphonyloxy.

A moreover also represents a hydroxyl, alkanoyloxy or alkoxy group, such as, for example, an acetoxy or methoxy group, in particular if compounds of the formula (I) in which $R^1$ is other than hydrogen are to be prepared with the aid of the process according to the invention.

The compounds of the formula (III) are generally known or obtainable in analogy to known processes (cf., for example, DE-A 20 40 175; DE-A 21 19 518; Synthesis 1973, 703).

Suitable diluents for carrying out the preparation process are inert organic solvents. These in particular include aliphatic, alicyclic or aromatic, optinally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide; esters, such as methyl acetate or ethyl acetate or bases such as pyridine, or organic acids such as formic acid or acetic acid.

The preparation process is preferably carried out in the presence of a suitable reaction auxiliary. Those suitable are all customary inorganic or organic bases. These include, for example, alkaline earth metal or alkali metal hydrides, hydroxides, amides, alcoholates, acetates, carbonates or hydrogencarbonates, such as, for example, sodium hydride, sodium amide, lithium diethylamide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonates or ammonium carbonate, organolithium compounds, such as n-butyllithium, and also tertiary amines, such as trimethylamine, triethylamine, tributylamine, diisopropylethylamine, tetramethylguanidine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

Alternatively, suitable reaction auxiliaries are also organic or inorganic acids, such as, for example, sulphuric acid, hydrochloric acid, p-toluenesulphonic acid, perfluorobutanesulphonic acid or strongly acidific ion exchangers, particularly if A represents a hydroxyl, acyloxy or alkoxy radical in the alkylating agents of the formual (III) used.

The preparation process can optionally also be carried out in a two-phase system, such as, for example, water/toluene or water/dichloromethane, if appropriate in the presence of a suitable phase-transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethyl-ammonium methylsulphate, dimethyl-$C_{12}/C_{14}$-alkyl-benzyl-ammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out the preparation process, the reaction temperatures can be varied within a relatively wide range. In general, the reaction is carried out at temperatures between −70° C. and +200° C., preferably at temperatures between 0° C. and 130° C.

The preparation process is customarily carried out under atmospheric pressure. However, it is also possible to work at increased or reduced pressure.

To carry out the preparation process, in general 1.0 to 5.0 mol, preferably 1.0 to 2.5 mol, of alkylating agent of the formula (III) and, if appropriate, 0.01 to 5.0 mol, preferably 1.0 to 3.0 mol, of reaction auxiliary are employed per mol of 1H-benzimidazole of the formula (II).

In a particular embodiment, it is also possible to silylate the 1H-benzimidazole of the formula (II) first in an earlier reaction step with the aid of customary silylation processes, for example using hexamethyldisilazane or trimethylsilyl chloride, if appropriate in the presence of a suitable catalyst, such as, for example, sulphuric acid, trifluoroacetic acid, ammonium sulphate, imidazole or saccharin at temperatures between −20° C. and +150° C. and to react the 1-trimethylsilylbenzimidazoles thus obtained in a subsequent second stage with alkylating agents of the formula (II) according to the preparation process. In this case, it is advantageous to add tin tetrachloride to the alkylation reaction as a catalyst (cf., for example, Chem. Heterocycl. Comp. USSR 24, 514 [1988]).

The reaction is carried out and worked up and the reaction products are isolated according to known processes (cf. Preparation Examples).

The final products of the formula (I) are purified with the aid of customary processes, for example by column chromatography or by recrystallization.

Characterization is carried out with the aid of the melting point or in the case of non-crystallizing compounds—in particular in the case of regioisomer mixtures—with the aid of proton nuclear magnetic resonance spectroscopy ($^1$H-NMR).

The active compounds have favourable mammalian toxicity and are suitable for the control of parasitic protozoa which occur in animal husbandry and animal breeding in the case of useful, breeding, zoo, laboratory and experimental animals and pets. At the same time, they are active against all or individual stages of development of the pests and also against resistant and normally sensitive strains. By means of the control of the parasitic protozoa, illness, cases of death and yield reductions (e.g. in the production of meat, milk, wool, hides, eggs, honey etc.) should be decreased, so that more economical and simpler animal husbandry is possible due to the use of the active compounds.

The parasitic protozoa include:

Mastigophora (Flagellata) such as, for example, Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example, *Giardia lamblia, G. canis.*

Sarcomastigophora (Rhizopoda) such as Entamoebidae, for example, *Entamoeba histolytica*, Hartmanellidae, for example, Acanthamoeba sp., Hartmanella sp.

Apicomplexa (Sporozoa) such as Eimeridae, for example, *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. niniakohlyakimovac, E. ovis, E. parva, E. pavonis, E. perforans, E. phasani, E. piriformis, E. praecox, E. residua, E. scabra*, E. spec., *E. stiedai, E. suis, E. tenella, E. truncata, E. truttae, E. zuernii*, Globidium spec., *Isospora belli, I. canis, I. felis, I. ohioensis, I. rivolta*, I. spec., *I. suis, Neospara caninum*, Cystisospora spec., Cryptosporidium spec. such as Toxoplasmadidae, for example, *Toxoplasma gondii*, such as Sarcocystidae, for example, *Sarcocystis bovicanis, S. bovihominis, S. ovicanis, S. ovifelis*, S. spec., *S. suihominis* such as Leucozoidae, for example, *Leucozytozoon simondi*, such as Plasmodiidae, for example, *Plasmodium berghei, P. falciparum, P. malariae, P. ovale, P. vivax*, P. spec., such as Piroplasmea, for example, *Babesia argentina, B. bovis, B. canis*, B. spec., *Theileria parva*, Theileria spec., such as Adeleina, for example, *Hepatozoon canis*, H. spec.

Furthermore Myxospora and Microspora, for example, Glugea spec. Nosema spec.

Furthermore Pneumocystis carinii, and also Ciliophora (Ciliata) such as, for example, *Balantidium coli*, Ichthiophthirius spec., Trichodina spec., Epistylis spec.

The compounds according to the invention are also active against protozoa which occur as parasites in insects. Those which may be mentioned are parasites of the strain Microsporida, in particular of the genus Nosema. Particular mention may be made of *Nosema apis* in the case of the honey bee.

The useful and breeding animals include mammals, such as, for example, cattle, horses, sheep, pigs, goats, camels, water buffalo, donkeys, rabbits, fallow deer, reindeer, fur-bearing animals such as, for example, mink, chinchilla, racoons, birds, such as, for example, hens, geese, turkeys, ducks, doves, bird species for keeping at home and in zoos. Useful and ornamental fish are furthermore included.

The laboratory and experimental animals include mice, rats, guinea pigs, golden hamsters, dogs and cats.

The pets include dogs and cats.

The fish include useful, breeding, aquarium and ornamental fish of all age levels, which live in fresh and salt water. The useful and ornamental fish include, for example, carps, eels, trout, whitefish, salmon, bream, roach, rudd, chub, sole, plaice, halibut, Japanese yellowtail *(Seriola quinqueradiata)*, Japanese eel *(Anguilla japonica)*, red seabream *(Pagurus major)*, seabass *(Dicentrarchus labrax)*, grey mullet *(Mugilus cephalus)*, pompano, gilthead seabream *(Sparus auratus)*, Tilapia ssp., Chichlidae species such as, for example, Plagioscion, Channel catfish. The compositions according to the invention are particularly suitable for the treatment of fry, e.g. carp of 2 to 4 cm body length. The compositions are also very highly suitable in eel feeding.

Administration can be carried out both prophylactically and therapeutically.

The administration of the active compounds is carried out directly or enterally, parenterally, dermally or nasally in the form of suitable preparations.

Enteral administration of the active compounds takes place, for example, orally in the form of powders, suppositories, tablets, capsules, pastes, drinks, granules, drenches, boli, medicated feed or drinking water. Dermal administration takes place, for example, in the form of dipping, spraying, bathing, washing, pouring on and spotting on, and dusting. Parenteral administration takes place, for example, in the form of injection (intramuscular, subcutaneous, intravenous, intraperitoneal) or by means of implants.

Suitable preparations are:

Solutions such as injection solutions, oral solutions, concentrates for oral administration after dilution, solutions for use on the skin or in body cavities, pour-on formulations, gels;

Emulsions and suspensions for oral or dermal administration and for injection; semi-solid preparations;

Formulations in which the active compound is incorporated in an ointment base or in an oil-in-water or water-in-oil emulsion base.

Solid preparations such as powders, premixes or concentrates, granules, pellets, tablets, boli, capsules; aerosols and inhalations, active compound-containing shaped articles.

Injection solutions are administered intravenously, intramuscularly and sub-cutaneously.

Injection solutions are prepared by dissolving the active compound in a suitable solvent and possibly adding additives such as solubilizers, acids, bases, buffer salts, antioxidants, preservatives. The solutions are sterile-filtered and buffered.

Solvents which may be mentioned are: physiologically tolerable solvents such as water, alcohols such as ethanol, butanol, benzyl alcohol, glycerol, hydrocarbons, propylene glycol, polyethylene glycols, N-methylpyrrolidone, and mixtures thereof.

If appropriate, the active compounds can also be dissolved in physiologically tolerable vegetable or synthetic oils which are suitable for injection.

Solubilizers which may be mentioned are: solvents which promote the dissolution of the active compound in the main solvent or prevent its precipitation. Examples are polyvinylpyrrolidone, polyethoxylated castor oil, polyethoxylated sorbitan ester.

Preservatives are: benzyl alcohol, trichlorobutanol, esters of p-hydroxybenzoic acid, n-butanol.

Oral solutions are administered directly. Concentrates are used orally after prior dilution to the use concentration. Oral solutions and concentrates arc prepared as described above in connection with injection solutions, it being possible to dispense with sterile operation.

Solutions for use on the skin are spotted on, painted on, rubbed in, squirted or sprayed on or applied by dipping, bathing or washing. These solutions are prepared as described above in connection with the injection solutions.

It may be advantageous to add thickeners during preparation. Thickeners are: inorganic thickeners such as bentonites, colloidal silica, aluminium monostearate, organic thickeners such as cellulose derivatives, polyvinyl alcohols and their copolymers, acrylates and methacrylates.

Gels are applied to or painted onto the skin or introduced into body cavities. Gels are prepared by mixing solutions, which have been prepared as described in connection with the injection solutions, with sufficient thickener to form a clear composition with an ointment-like consistency. Thickeners employed are the thickeners indicated further above.

Pour-on formulations are poured or squirted onto limited areas of the skin, the active compound either penetrating the skin and acting systemically or being dispersed on the surface of the body.

Pour-on formulations are prepared by dissolving, suspending or emulsifying the active compound in suitable skin-tolerable solvents or solvent mixtures. If appropriate, further auxiliaries such as colorants, absorption-promlloting substances, antioxidants, sunscreen agents, adherents are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetal or synthetic oils, DMF, dimethylacetamide, N-methylpyrrolidone, 2-dimethyl-4-oxy-methylene-1,3-dioxolane.

Colorants are all colorants approved for use on animals and which can be dissolved or suspended.

Absorption-promoting substances are, for example, DMSO, spreading oils such as isopropyl myristate, dipropylene glycol pelargonate, silicone oils, esters of fatty acids, triglycerides, fatty alcohols.

Antioxidants are sulphites or metabisulphites such as potassium metabisulphite, ascorbic acid, butylhydroxytoluene, butylhydroxyanisole, tocopherol.

Sunscreen agents are, for example, substances from the benzophenones or novantisolic acid class.

Adherents are, for example, cellulose derivatives, starch derivatives, polyacrylates, natural polymers such as alginates, gelatine.

Emulsions can be used orally, dermally or as injections.

Emulsions are either of the type water-in-oil or of the type oil-in-water.

They are prepared by dissolving the active compound either in the hydrophobic or in the hydrophilic phase and homogenizing this with the solvent of the other phase with the aid of suitable emulsifiers and, if appropriate, further auxiliaries such as colorants, absorption-promoting substances, preservatives, antioxidants, sunscreen agents, viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixtures with vegetable fatty acids of chain length $C_{8-12}$ or other specially selected natural fatty acids, partial glyceride mixtures of saturated or unsaturated fatty acids possibly also containing hydroxyl groups, mono- and diglycerides of the $C_8/C_{10}$ fatty acids.

Esters of fatty acids such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleates, decyl oleates, ethyl oleate, ethyl lactates, waxy fatty acid esters such as dibutyl phthalate, diisopropyl adipate, ester mixtures related to the latter, inter alia fatty alcohols such as isotridecyl alcohol, 2-octyldodecanol, cetylstearyl alcohol, oleyl alcohol.

Fatty acids such as, for example, oleic acid and its mixtures.

Hydrophilic phases which may be mentioned are:

water, alcohols such as, for example, propylene glycol, glycerol, sorbitol and their mixtures.

Emulsifiers which may be mentioned are:

nonionic surfactants, e.g. polyethoxylated castor oil, polyethoxylated sorbitan monooleate, sorbitan monostearate, glycerol monostearate, polyoxyethyl stearate, alkylphenyl polyglycol ethers;

ampholytic surfactants such as di-Na N-lauryl-β-iminodipropionate or lecithin;

anionic surfactants, such as Na laurylsulphates, fatty alcohol ether sulphates, mono/dialkyl polyglycol ether orthophosphate monoethanolamine salt;

cationic surfactants such as cetyltrimethylammonium chloride.

Further auxiliaries which may be mentioned are:

viscosity-increasing and emulsion-stabilizing substances such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions can be used orally, dermally or as an injection. They are prepared by suspending the active compound in a suspending agent, if appropriate with addition of further auxiliaries such as wetting agents, colorants, absorption-promoting substances, preservatives, antioxidants, sunscreen agents.

Suspending agents which may be mentioned are all homogeneous solvents and solvent mixtures.

Wetting agents (dispersing agents) which may be mentioned are the surfactants indicated further above.

Further auxiliaries which may be mentioned are those indicated further above.

Semi-solid preparations can be administered orally or dermally. They differ from the suspensions and emulsions described above only by their higher viscosity.

To prepare solid preparations, the active compound is brought into the desired form with suitable excipients, if appropriate with addition of auxiliaries.

Excipients which may be mentioned are all physiologically tolerable solid inert substances. Those which are used are inorganic and organic substances. Inorganic substances are, for example, sodium chloride, carbonates such as calcium carbonate. hydrogencarbonates, aluminium oxides, silicicas, argillaceous earths, precipitated or colloidal silica, phosphates.

Organic substances are, for example, sugar, cellulose, foodstuffs and feedstuffs such as powdered milk, animal meals, cereal meals and shreds, starches.

Auxiliaries are preservatives, antioxidants, colorants which have already been mentioned further above.

Further suitable auxiliaries are lubricants and glidants such as, for example, magnesium stearate, stearic acid, talc, bentonites, disintegration-promoting substances such as starch or crosslinked polyvinyl pyrrolidone, binding agents such as, for example, starch, gelatine or linear polyvinylpyrrolidone and also dry binding agents such as microcrystalline cellulose.

The active compounds can be present in the preparations even as a mixture with synergists or with other active compounds.

Particular emphasis may be given to mixtures of the compounds according to the invention with a polyether antibiotic or a synthetically prepared coccidiosis agent.

Synthetic coccidiosis agents or polyether antibiotics which may preferably be mentioned for use in the mixtures according to the invention are:

Amprolium, in some cases in combination with folic acid antagonists

Robenidine

Toltrazuril

Monensin

Salinomycin

Maduramicin.

Particular emphasis may be given to the mixture with maduramicin.

Ready-to-use preparations contain the active compounds in concentrations of 10 ppm to 20 percent by weight, preferably from 0.1 to 10 percent by weight.

Preparations which are diluted before use contain the active compound in concentrations from 0.5 to 90 percent by weight, preferably from 1 to 50 percent by weight.

In general, it has proved advantageous to administer amounts from approximately 0.5 to approximately 50 mg, preferably 1 to 20 mg, of active compound per kg of body weight per day to achieve effective results.

In the mixture with other coccidiosis agents or polyether antibiotics, the active compounds according to the invention are in the ratio 1 to 0.1–10 to 1 to 1–10. The ratio 1 to 5 is preferred.

The active compounds can also be administered to the animals together with the feed or drinking water.

Feedstuffs and foodstuffs contain 0.01 to 250 ppm, preferably 0.5 to 100 ppm, of the active compound in combination with a suitable edible material.

Such a feedstuff and foodstuff can be used both for curative purposes and for prophylactic purposes.

Such a feedstuff or foodstuff is prepared by mixing a concentrate or a premix which contains 0.5 to 30%, preferably 1 to 20%, by weight of an active compound as a mixture with an edible organic or inorganic carrier with customary feedstuffs. Edible carriers are, for example, maize flour or maize and soya bean flour or mineral salts, which preferably contain a small amount of an edible dust prevention oil, e.g. maize oil or soya oil. The premix obtained in this way can then be added to the complete feedstuff before feeding it to the animals.

By way of example, use in coccidiosis may be mentioned:

For the healing and prophylaxis, for example, of coccidiosis in poultry, in particular in hens, ducks, geese and turkeys, 0.1 to 100 ppm, preferably 0.5 to 100 ppm, of an active compound are mixed with a suitable edible material, e.g. a nutritious feedstuff. If desired, these amounts can be increased, particularly if the active compound is well tolerated by the recipient. Correspondingly, administration can be carried out via the drinking water.

For the treatment of individual animals, e.g. in the case of the treatment of coccidiosis in mammals or of toxoplasmosis, amounts of active compound of 0.5 to 100 mg/kg of body weight are preferably administered daily in order to achieve the desired results. In spite of this, it may occasionally be necessary to depart from the amounts mentioned, in particular depending on the body weight of the experimental animal or on the type of administration method, but also because of the animal genus and its individual reaction to the active compound or the nature of the formulation and the time or the interval at which it is administered. Thus in certain cases it may be sufficient to manage with less than the abovementioned minimum amount, while in other cases the upper limit mentioned must be exceeded. When administering relatively large amounts, it may be advisable to divide these into several individual administrations during the course of the day.

The efficacy of the compounds according to the invention can be confirmed, for example, in cage experiments with the following experimental arrangement, in which the animals are treated with the respective individual components and with the mixtures of the individual components.

An active compound-containing feed is prepared such that the required amount of active compound is basically mixed with a nutritionally balanced animal feed, e.g. with the chick feed indicated below.

If a concentrate or a premix is to be prepared, which is finally to be diluted in the feed to the values mentioned in the experiment, in general approximately 1 to 30%, preferably approximately 10 to 20% by weight, of active compound are mixed with an edible organic or inorganic carrier, e.g. maize and soya meal or mineral salts which contain a small amount of an edible dedusting oil, e.g. maize oil or soya bean oil. The premix thus obtained can then be added to the complete poultry feed before administration.

A suitable example of the use of the substances according to the invention in the poultry feed is the following composition.

| | |
|---|---|
| 52.00% | of feed cereal shreds, mainly: 40% maize, 12% wheat |
| 17.00% | of soya shreds extr. |
| 5.00% | of maize gluten feed |
| 5.00% | of wheat feed meal |
| 3.00% | of fish meal |
| 3.00% | of mineral mixture |
| 3.00% | of alfalfa meal |
| 2.50% | of vitamin premix |
| 2.00% | of wheat germs, comminuted |
| 2.00% | of soya oil |
| 2.00% | of meat and bone meal |
| 1.50% | of whey powder |
| 1.00% | of molasses |
| 1.00% | of brewer's yeast, bound to brewer's gains |
| 100.00% | |

Such a feed contains 18% raw protein, 5% raw fibre, 1% Ca, 0.7% P and, per kg, 1200 I.U. of vitamin A, 1200 I.U. of vitamin D3, 10 mg of vitamin E, 20 mg of zinc bacitracin.

Cage Experiment on Coccidiosis/Chicks 8 to 12 day-old male chicks (e.g. LSL Brinkschulte/Senden) which have been reared coccidia-free receive the compounds according to the invention (test substances) in the concentration indicated in ppm with the feed from 3 days before (day −3) infection (=a.i.) until 8 (9) days after infection (=p.i.). 3 animals are kept in each cage. One or more groups of this type are employed per dose. Infection is carried out by means of a stomach tube directly into the crop with approximately 100,000 sporulated oocysts of *Eimeria acervulina* and with approximately 30,000 oocysts each of *E. maxima* and 40,000 sporulated oocysts of *E. tenella*. These are highly virulent strains. The exact infection dose is adjusted so that, if possible, one of three experimentally infected untreated chicks dies due to the infection. For assessment of the efficacy, the following criteria are taken into account: weight increase from the start of the experiment to the end of the experiment, death rate due to infection, macroscopic assessment of the faeces with respect to diarrhoea and excretion of blood on days 5 and 7 p.i. (assessment 0 to 6), macroscopic assessment of the intestinal mucosa, in particular of the appendices (assessment 0 to 6) and the oocyst excretion as well as the proportion (in %) of the oocysts sporulating in the course of 24 hours. The number of oocysts in the faeces was determined with the aid of a McMaster counting chamber (see Engelbrecht and coworkers "Parasitologische Arbeitsmethoden in Medizin and Veterinärmedizin" [Parasitological Working Methods in Medicine and Veterinary Medicine], Akademie-Verlag, Berlin (1965)). The individual findings are related to the untreated non-infected control groups and a total score is calculated (cf. A. Haberkorn (1986), pp. 263 to 270 in Research in Avian Coccidiosis ed L. R. McDougald, L. P. Joyner, P. L. Long, Proceedings of the Georgia Coccidiosis Conference, Nov. 18–20, 1985. Athens/Georgia USA).

Experimental results with combinations according to the invention are shown by way of example in the following tables. The synergistic activity of the combinations in comparison with the individual components is particularly evident in the reduction of oocysts excretion but also with respect to the section findings, weight gain and better tolerability.

In the following tables, in the column "Treatment" the information means n.inf.contr.=non-infected control group inf.contr.=infected control group 1=benzimidazole example No.

In the column "ppm", the concentration of the active compound employed in the feed is indicated in ppm.

In the column "mortality" the percentage of the dead animals is indicated under % and the number of dead animals/animals employed in the experiment is indicated under n.

In the column "weight % of not inf. control" the ratio of the weight of the treated animals to the weight of the non-infected control group is indicated.

In the columns "dropping scores", "lesion score" and "oocyst control", individual details of the action are given.

In the column "% efficacy", the total score is assessed; 0% means no action, 100% means full action.

TABLE 1

Experimental infection with *Eimeria acervulina*, *Eimeria maxima* and *Eimeria tenella* in chicks. Ex. 1 in combination with monensin.

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| n.inf.contr. | 0 | 0 | 0/6 | 100 | 0 | 0 | 0 | 0 | 0 | 0 | 100 |
| inf.contr. | 0 | 100 | 6/6 | 0 | 6 | 6 | 100 | 100 | 100 | 100 | 0 |

TABLE 1-continued

Experimental infection with *Eimeria acervulina*, *Eimeria maxima* and *Eimeria tenella* in chicks. Ex. 1 in combination with monensin.

| Treatment | ppm | mortality % | mortality n | weight % of not inf. control | drop-ping scores | lesion score | oocyst in % of inf. control ac. | max. | ten. | tot. | % effi-cacy tot. |
|---|---|---|---|---|---|---|---|---|---|---|---|
| Ex. 1 | 7.5 | 0 | 0/3 | 76 | 6 | 5.3 | 3 | 0 | 1 | 1.3 | 65 |
| Ex. 1 | 10 | 0 | 0/3 | 84 | 6 | 3.3 | 0 | 0 | 1 | 0 | 75 |
| Mon. | 25 | 33 | 1/3 | 36 | 6 | 6 | 98 | 0 | 100 | 66 | 45 |
| Mon. | 50 | 33 | 1/3 | 81 | 6 | 6 | 44 | 0 | 13 | 19 | 36 |
| Mon. | 100 | 33 | 1/3 | 30 | 6 | 6 | 8 | 0 | 100 | 36 | 24 |
| Ex. 1 + Mon. | 7.5 + 25 | 0 | 0/3 | 93 | 6 | 0 | 0 | 0 | 2 | 0.6 | 88 |
| Ex. 1 + Mon. | 10 + 25 | 33 | 1/3 | 95 | 3 | 0.5 | 0 | 0 | 0 | 0 | 100 |
| Ex. 1 + Mon. | 7.5 + 50 | 0 | 0/3 | 100 | 0 | 1.7 | 0 | 0 | 0 | 0 | 100 |
| Ex. 1 + Mon. | 10 + 50 | 0 | 0/3 | 95 | 0 | 0.7 | 0 | 0 | 0 | 0 | 100 |
| Ex. 1 + Mon. | 7.5 + 100 | 33 | 1/3 | 114 | 0 | 0 | 0 | 0 | 0 | 0 | 100 |
| Ex. 1 + Mon. | 10 + 100 | 0 | 0/3 | 99 | 0 | 0 | 0 | 0 | 0 | 0 | 100 |

TABLE 2

Experimental infection with *Eimeria acervulina*, *Eimeria maxima* and *Eimeria tenella* in chicks. Ex. 1 in combination with maduramicin.

| Treatment | ppm | mortality % | mortality n | weight % of not inf. control | drop-ping scores | lesion score | oocyst in % of inf. control ac. | max. | ten. | tot. | % effi-cacy tot. |
|---|---|---|---|---|---|---|---|---|---|---|---|
| n.inf.contr. | 0 | 0 | 0/6 | 100 | 0 | 0 | 0 | 0 | 0 | 0 | 100 |
| inf.contr. | 0 | 50 | 3/6 | 58 | 6 | 6 | 100 | 100 | 100 | 100 | 0 |
| Ex. 1 | 1 | 33 | 1/3 | 31 | 6 | 6 | 49 | 100 | 97 | 82 | 36 |
| Ex. 1 | 2.5 | 33 | 1/3 | 42 | 4–6 | 6 | 19 | 100 | 55 | 58 | 36 |
| Ex. 1 | 5 | 0 | 0/3 | 110 | 1 | 0 | 1 | 100 | 11 | 37 | 90 |
| MAD | 1 | 0 | 0/3 | 93 | 1 | 2 | 8 | 100 | 30 | 46 | 73 |
| MAD | 2 | 0 | 0/3 | 114 | 0 | 2 | 8 | 100 | 45 | 51 | 84 |
| MAD | 3 | 0 | 0/3 | 112 | 0 | 0 | 1 | 0 | 3 | 1.3 | 100 |
| Ex. 1 + MAD | 2.5 + 1 | 0 | 0/3 | 122 | 0 | 0 | 0 | 0 | 0 | 0 | 100 |
| Ex. 1 + MAD | 5 + 1 | 0 | 0/3 | 119 | 0 | 0 | 0 | 0 | 0 | 0 | 100 |
| Ex. 1 + MAD | 2.5 + 2 | 0 | 0/3 | 122 | 0 | 0 | 0 | 0 | 0 | 0 | 100 |
| Ex. 1 + MAD | 5 + 2 | 0 | 0/3 | 105 | 0 | 0 | 0 | 0 | 0 | 0 | 100 |
| Ex. 1 + MAD | 2.5 + 3 | 0 | 0/3 | 117 | 0 | 0 | 0 | 0 | 0 | 0 | 100 |
| Ex. 1 + MAD | 1 + 3 | 0 | 0/3 | 121 | 0 | 0 | 0 | 0 | 0 | 0 | 100 |

TABLE 3

Experimental infection with *Eimeria acervulina*, *Eimeria maxima* and *Eimeria tenella* in chicks. Ex. 1 in combination with salinomycin.

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n.inf.contr. | 0 | 0 | 0/6 | 100 | 0 | 0 | 0 | 0 | 0 | 0 | 100 |
| inf.contr. | 0 | 100 | 6/6 | 0 | 6 | 6 | 100 | 100 | 100 | 100 | 0 |
| Ex. 1 | 5 | 0 | 0/3 | 72 | 6 | 6 | 6 | 0 | 30 | 12 | 45 |
| Ex. 1 | 7.5 | 0 | 0/3 | 76 | 6 | 5.3 | 3 | 0 | 1 | 1.3 | 65 |
| Ex. 1 | 10 | 0 | 0/3 | 84 | 6 | 3.3 | 0 | 0 | 1 | 0 | 75 |
| Sal. | 15 | 100 | 3/3 | T | T | T | T | T | T | T | T |
| Sal. | 30 | 100 | 3/3 | T | T | T | T | T | T | T | T |
| Sal. | 60 | 0 | 0/3 | 106 | 6 | 1.3 | 6 | 0 | 31 | 12 | 67 |
| Ex. 1 + Sal | 7.5 + 15 | 0 | 0/3 | 107 | 0 | 0 | 0 | 0 | 0 | 0 | 100 |
| Ex. 1 + Sal | 10 + 15 | 33 | 1/3 | 103 | 0 | 0 | 0 | 0 | 0 | 0 | 100 |
| Ex. 1 + Sal | 5 + 30 | 0 | 0/3 | 121 | 0 | 0 | 0 | 0 | 0 | 0 | 100 |
| Ex. 1 + Sal | 10 + 30 | 33 | 1/3 | 103 | 0 | 0 | 0 | 0 | 0 | 0 | 100 |
| Ex. 1 + Sal | 5 + 60 | 0 | 0/3 | 91 | 2 | 0 | 0 | 0 | 0 | 0 | 100 |
| Ex. 1 + Sal | 10 + 60 | 33 | 1/3 | 97 | 0 | 0 | 0 | 0 | 0 | 0 | 100 |

The results of the efficacy experiments with the compounds according to the invention are summarized in the following table:

TABLE 4

Efficacy against *Eimeria acervulina*, *Eimeria maxima* and *Eimeria tenella*

| Compound | Dose in ppm | | |
|---|---|---|---|
| | 10 | 5 | 2.5 |
| Ex. 1 | 2 2 2 | 2 2 2 | 1 1 1 |
| Ex. 2 | D D D | 2 2 2 | 1 2 1 |
| Ex. 3 | 2 2 2 | 2 2 2 | 0 2 1 |
| Ex. 4 | 1 1 1 | 1 1 1 | 1 2 1 |
| Ex. 5 | 1 1 2 | 1 1 1 | 1 2 1 |
| Ex. 6 | 2 2 2 | 2 2 2 | 1 1 1 |
| Ex. 7 | 2 2 1 | 2 2 2 | 2 1 2 |
| Ex. 8 | 2 2 2 | 0 1 1 | 0 0 0 |
| Ex. 9 | 2 2 2 | 2 2 1 | 0 1 1 |

Assessment Scheme:

2=full action

1=slight action

0=inactive

D=death

The following preparation examples are intended to illustrate but not to restrict the present invention:

EXAMPLE 1

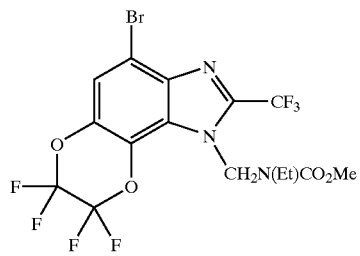

39.0 g (0.1 mol) of 4-bromo-6,7-tetrafluoro-6,7-dihydro-2-trifluoromethyl-1H-[1,4]-dioxino[2,3-e]benzimidazole is introduced into 1000 ml of $CH_2Cl_2$, 17.5 ml (0.125 mol) of triethylamine are added and 18.9 g (0.125 mol) of methyl N-chloromethyl-N-ethyl-carbamate are added dropwise at 20° C. and the mixture is refluxed for 24 h. It is washed twice with 250 ml each of water and with 250 ml of saturated, aqueous sodium chloride solution and dried over sodium sulphate. The residue obtained after evaporation (54.4 g) is chromatographed on 1 kg of silica gel (35–70 μm) using cyclohexane/ethyl acetate (10:1).

Yield: 30.6 g (60% of theory), m.p.: 92–93° C.

Example 2–12 Below of the Formula

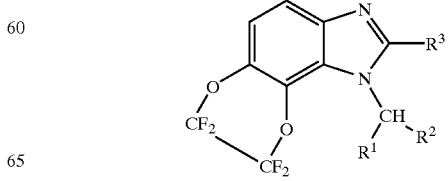

were obtained analogously to Example 1 and according to the general instructions for preparation.

Yield: 396 g (98% of theory), (crude, GC: 99.1%), b.p.$_{16}$: 121–124° C., $n_D$: 1.5065 at 20° C.

| Example No. | X$^1$ | R$^1$ | R$^2$ | R$^3$ | M.p. [° C.] | $^1$H-NMR(CDCl$_3$): δ[ppm] |
|---|---|---|---|---|---|---|
| 2 | Br | H | CH$_2$N(Me)CO$_2$Me | CF$_3$ | | 2.8(s, 3H), 6.07(s, 2H) |
| 3 | Cl | H | CH$_2$N(Me)CO$_2$Me | CF$_3$ | 72–74 | |
| 4 | Cl | H | CH$_2$N(Et)CO$_2$Me | CF$_3$ | | 0.97(t, 3H), 3.80(s, 3H), 7.26(s, 1H), |
| 5 | Br | H | CH$_2$N(Bu)CO$_2$Et | CF$_3$ | | 0.76(t, 3H), 3.06(q, 2H), 6.08(s, 2H), |
| 6 | Br | H | CH$_2$N(iPr)CO$_2$Et | CF$_3$ | | 1.13(d, 6H), 3.32(sept., 1H), 6.06(s, 2H), |
| 7 | Cl | H | CH$_2$N(iPr)CO$_2$Et | CF$_3$ | | 1.15(d, 6H), 3.38(sept., 1H) 6.12(s, 2H) |
| 8 | Cl | H | CH$_2$N(2-Me—C$_6$H$_4$)CO$_2$Me | CF$_3$ | 134–136 | |
| 9 | Cl | H | CH$_2$N(C$_6$H$_{11}$)CO$_2$Et | CF$_3$ | 85–88 | |
| 10 | Br | H | CH$_2$N(2-Me—C$_6$H$_4$)CO$_2$Me | CF$_3$ | 135–136 | |
| 11 | Cl | H | CH$_2$N(Pr)CO$_2$Et | CF$_3$ | | 0.77(t, 3H) 4.23(q, 2H) 6.14(s, 2H) |

Me = Methyl
Bu = n-Butyl
Et = Ethyl
iPr = iso-Propyl
Pr = n-Propyl

The preparation of the starting compound for Examples 1, 2, 6 and 8 can be carried out as indicated below:

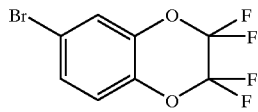

1400 g (6.7 mol) of 2,3-tetrafluoro-1,4-benzodioxane and 7 g (0.08 mol) of FeS (powder) are introduced, 1190 g (7.4 mol) of bromine are added dropwise at 20 to 30° C. in the course of about 4 h and the mixture is stirred for about 20 h until evolution of gas is complete. It is washed with aqueous sodium sulphite solution and dried over sodium sulphate. The residue is distilled in vaeuo.

Yield: 1540 g (80% of theory), b.p.$_{10}$: 70–74° C. (GC: 99%).

Example b)

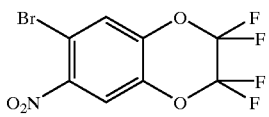

350 g (1.2 mol) of 6-bromo-2,3-tetrafluoro-1,4-benzodioxane are added dropwise at 20° C. in the course of 75 min to 273 ml (98% strength) of nitric acid and 293 ml of conc. sulphuric acid, and the reaction mixture is stirred at 20° C. for 1 h and at 40° C. for 3 h. The mixture is poured onto ice, extracted with methylene chloride, and the organic phase is washed with water and with aqueous sodium hydrogencarbonate solution and dried over sodium sulphate. The organic phase is evaporated and reacted further as a crude product.

Example c)

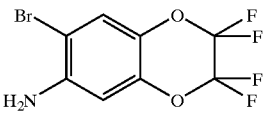

396 g (1.2 mol) of 6-bromo-7-nitro-2,3-tetrafluoro-1,4-benzodioxane are introduced into 1400 ml of ethanol, 253 g (4.5 mol) of Fe powder are added and the mixture is heated to reflux. 29 g of conc. hydrochloric acid are then added dropwise under reflux and the mixture is stirred for 1 h, 43 ml of water are added dropwise at boiling heat and the reaction mixture is stirred for 2 h. The mixture is cooled, and the precipitate is filtered off with suction and washed with ethanol. The mother liquor is rendered alkaline and evaporated. The residue is taken up in methylene chloride and washed twice with water and dried over sodium sulphate. The organic phase is evaporated.

Yield: 313 g (87% of theory), (GC: 95.3%).

Example d)

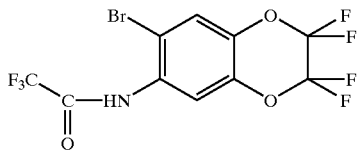

313 g (1.04 mol) of 7-amino-6-bromo-2,3-tetrafluoro-1 4-benzodioxane are introduced into 1250 ml of toluene and 500 g (4.4 mol) of trifluoroacetic acid, and 188 g (1.3 mol) of phosphorus pentoxide are added in portions at 20 to 25° C. the mixture becomes lumpy. It is heated at 80° C. for 1 h (not stirrable): the mixture is treated with 500 ml of water and stirred for a further 1 h at 80° C. After cooling, the organic phase is separated off and dried over sodium sulphate. The evaporated residue (340 g) still contains 50% starting material (GC).

The residue (340 g, 50% pure) is therefore again treated with 1250 ml of toluene and 500 g (4.4 mol) of trifluoroacetic acid, then 188 g (1.3 mol) of phosphorus pentoxide are added in portions and the mixture is heated at 80° C. for 5 h. The organic phase is decanted off, washed twice with water, dried over sodium sulphate and evaporated.

Yield: 273 g (66% of theory), m.p.: 79–81° C. (GC: 98%)

The lumpy reaction residue is treated with water, and the organic portion is separated off, dried over sodium sulphate and evaporated.

Yield: 56 g (14%), (GC: 87%).

Example e)

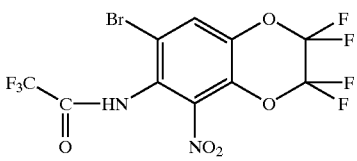

273 g (0.7 mol) of 6-bromo-7-trifluoromethylcarbonylamino-2,3-tetrafluoro-1,4-benzodioxane are introduced into 2047 ml of conc. sulphuric acid and 300 g of mixed at 0 to 20° C. with 1000 ml of methylene chloride. The solution is then stirred at 40° C. for 2 h. The cooled contents of the flask are poured onto ice water and the precipitate is isolated. The organic phase is separated off from the mother liquor and dried over sodium sulphate. The evaporated residue and the isolated precipitate are combined.

Yield: 269 g (88% of theory), m.p.: 158–159° C. (GC: 100%).

Example f)

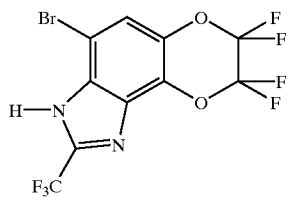

347 g (0.8 mol) of 6-bromo-8-nitro-7-trifluoromethylcarbonylamino-2,3-tetrafluoro-1,4-benzodioxane are introduced into 1735 ml of ethanol and 183 g (3.3 mol) of Fe filings and 183 g (3.3 mol) of Fe powder are added. 38.5 ml of hydrochloric acid are added dropwise under reflux, the mixture is stirred for 1 h, then 58 ml of water are added dropwise and it is refluxed for 15 h. The cooled mixture is filtered off with suction, and the mother liquor is rendered alkaline and evaporated. The residue is taken up in methylene chloride, washed twice with water, dried over sodium sulphate and evaporated. The residue (170 g) is chromatographed on 1 kg of silica gel (35–70 μm) using cyclohexane/ethyl acetate (5:1).

Yield: 125 g (40% of theory), m.p. 162–164° C.

The compound of example f) obtainable in this way can optionally be reacted further without further purification by alkylation to the compounds according to the invention.

What is claimed is:

1. A benzimidazole of the formula (I)

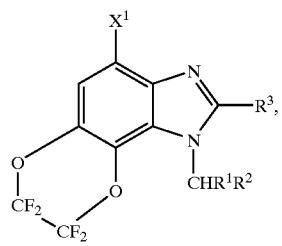

in which $X^1$ represents chlorine or bromine, $R^1$ represents hydrogen or $C_{1-4}$-alkyl, $R^3$ represents fluoro-$C_{1-4}$-alkyl, $R^2$ represents the radical

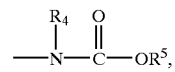

$R^4$ represents $C_{1-6}$-alkyl or phenyl optionally substituted with $C_{1-4}$-alkyl, $C_{1-4}$-halogenoalkyl, $C_{1-4}$-alkoxy, or $C_{1-4}$-halogenoalkoxy, $R^5$ represents $C_{1-4}$-alkyl.

2. Process for the preparation of a benzimidazole of the formula (I)

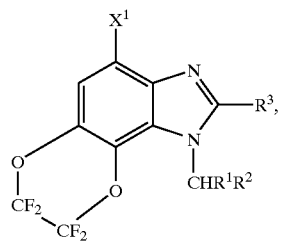

in which $X^1$ represents chlorine or bromine $R^1$ represents hydrogen or $C_{1-4}$-alkyl, $R^3$ represents fluoro-$C_{1-4}$-alkyl, $R^2$ represents the radical

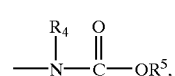

$R^4$ represents $C_{1-6}$-alkyl or phenyl optionally substituted with $C_{1-4}$-alkyl, $C_{1-4}$-halogenoalkyl, $C_{1-4}$-alkoxy, or $C_{1-4}$-halogenoalkoxy, $R^5$ represents $C_{1-4}$-alkyl, characterized in that 1H-benzimidazoles of the formula (II)

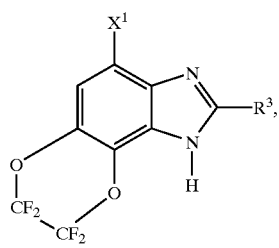
(II)

in which
X$^1$ and R$^3$ have the meaning indicated above,
are reacted with an alkylating agent of the formula (III)

$$A\text{—}CHR^1R^2 \quad (III),$$

in which
A represents a suitable leaving group selected from the group consisting of halogen, hydroxyl, alkylsulphonyloxy, alkoxysulphonyloxy, arylsulphonyloxy, alkanoyloxy, and alkoxy,
R$^1$ and R$^2$ have the meaning indicated above.

3. A composition against parasitic protozoa, comprising a substituted benzimidazole of the formula (I) according to claim 1, in combination with an inert carrier.

4. A process for controlling parasitic protozoa, characterized in that an effective amount of a substituted benzimidazole of the formula (I) according to claim 1 is administered to an animal.

* * * * *